(12) United States Patent
Rajaraman et al.

(10) Patent No.: US 9,700,221 B2
(45) Date of Patent: Jul. 11, 2017

(54) NON-INVASIVE SEGMENTABLE THREE-DIMENSIONAL MICROELECTRODE ARRAY PATCH FOR NEUROPHYSIOLOGICAL DIAGNOSTICS AND THERAPEUTIC STIMULATION

(71) Applicant: Axion BioSystems, Inc., Atlanta, GA (US)

(72) Inventors: Swaminathan Rajaraman, Atlanta, GA (US); Julian A. Bragg, Decatur, GA (US); James D. Ross, Decatur, GA (US); Amanda Preyer, Atlanta, GA (US)

(73) Assignee: Axion BioSystems, Inc., Atlanta, GA (US)

( * ) Notice: Subject to any disclaimer, the term of this patent is extended or adjusted under 35 U.S.C. 154(b) by 636 days.

(21) Appl. No.: 14/199,580

(22) Filed: Mar. 6, 2014

(65) Prior Publication Data

US 2014/0303471 A1   Oct. 9, 2014

Related U.S. Application Data

(60) Provisional application No. 61/773,237, filed on Mar. 6, 2013.

(51) Int. Cl.
*A61B 5/04* (2006.01)
*A61N 1/05* (2006.01)
(Continued)

(52) U.S. Cl.
CPC .......... *A61B 5/04001* (2013.01); *A61B 5/685* (2013.01); *A61B 5/6833* (2013.01);
(Continued)

(58) Field of Classification Search
CPC .......................... A61B 5/04001; A61N 1/0502
(Continued)

(56) References Cited

U.S. PATENT DOCUMENTS 4,969,468 A * 11/1990 Byers ................... A61B 5/0422
                                                         29/829
5,215,088 A    6/1993 Normann et al.
(Continued)

OTHER PUBLICATIONS

Alarcon, J., et al., "Preclinical Evaluation of Microneedle Technology for Intradermal Delivery of Influenza Vaccines," Clinical and Vaccine Immunology, 2007, vol. 14, No. 4, pp. 375-381.
(Continued)

*Primary Examiner* — Lee S Cohen
(74) *Attorney, Agent, or Firm* — Meunier Carlin & Curfman LLC

(57) ABSTRACT

Implementations disclosed herein provide for a microneedle electrode system comprising a microneedle electrode patch connected to external electronics. The microneedle electrode patch comprises a first flexible substrate having a plurality of conductive pads disposed thereon, a plurality of three-dimensional, individually addressable microneedle electrode arrays where each array has a plurality of microneedles extending from an upper surface thereof and a lower surface adapted to contact a corresponding one of the plurality of conductive pads disposed on the first substrate, and a second flexible substrate having a plurality of openings defined therein dimensioned to accommodate at least a portion of the upper surface of the microneedle electrode array from which the microneedles extend. Each of the conductive pads is disposed in electrical communication with a corresponding one of the plurality of microneedle electrode arrays and the first and second substrate are bonded together such that each one of the plurality of microneedle electrode arrays extends
(Continued)

through a corresponding one of the plurality of openings defined in the second substrate.

37 Claims, 11 Drawing Sheets

(51) Int. Cl.
  *A61B 5/00* (2006.01)
  *A61N 1/04* (2006.01)
(52) U.S. Cl.
  CPC ...... *A61N 1/0502* (2013.01); *A61B 2562/222* (2013.01); *A61N 1/0452* (2013.01); *A61N 1/0456* (2013.01); *A61N 1/0476* (2013.01); *A61N 1/0492* (2013.01)
(58) Field of Classification Search
  USPC .................................................. 600/373, 377
  See application file for complete search history.

(56) References Cited

U.S. PATENT DOCUMENTS

| | | | | |
|---|---|---|---|---|
| 6,151,519 | A * | 11/2000 | Sugihara | A61N 1/0456 204/403.01 |
| 6,690,959 | B2 * | 2/2004 | Thompson | A61B 5/0006 600/372 |
| 6,745,062 | B1 * | 6/2004 | Finneran | A61B 5/04004 600/382 |
| 7,359,744 | B2 * | 4/2008 | Lee | A61B 5/04085 600/391 |
| 8,359,083 | B2 | 1/2013 | Clark et al. | |
| 8,781,576 | B2 * | 7/2014 | Savage | A61N 1/39 607/5 |
| 9,173,583 | B2 * | 11/2015 | Chen | A61B 5/0478 |
| 9,248,273 | B2 * | 2/2016 | Guvanasen | A61N 1/0502 |
| 2008/0138581 | A1 | 6/2008 | Bhandari et al. | |
| 2008/0138583 | A1 | 6/2008 | Bhandari et al. | |

OTHER PUBLICATIONS

Allen, D.M., "Photochemical Machining: from 'manufacturing's best kept secret' to a $6 billion per annum rapid manufacturing process," CIRP Annals—Manufacturing Technology, vol. 53, No. 2, 2004, pp. 559-572.

Bartels, J., et al., "Neurotrophic Electrode: Method of assembly and implantation into human speech cortex," Journal of Neuroscience Methods, vol. 174, No. 2, 2008, pp. 168-176.

Bhadra, N., et al., "High Frequency Electrical Conduction Block of Mammalian Peripheral Motor Nerve," Muscle Nerve, vol. 32, No. 6, 2005, pp. 782-790.

Blum, R. A., et al., "An Integrated System for Simultaneous, Multichannel Neuronal Stimulation and Recording," IEEE Transactions on Circuits and Systems I: Regular Papers, vol. 54, No. 12, 2007, pp. 2608-2618.

Bozon, J.P., et al., "Development of Metal-Based Microelectrode Sensor Platforms by Chemical Vapor Deposition," Electroanalysis, vol. 13, No. 11, 2001, pp. 911-916.

Brown, E.A., et al., "Stimulus-Artifact Elimination in a Multi-Electrode System," IEEE Transactions on Biomedical Circuits and Systems, vol. 2, No. 1, 2008, pp. 10-21.

Choi, S-O., et al, "An Electrically Active Microneedle Array for Electroporation of Skin for Gene Delivery," IEEE Transducers'05, 2005, pp. 1513-1516.

Davis, S.P., et al., "The Mechanics of Microneedles," Proceedings of the Second Joint EMBS/BMES Conferences, 2002, pp. 498-499.

Gill, H.S., et al., "Coated microneedles for transdermal delivery," Journal of Controlled Release, vol. 117, 2007, pp. 227-237.

Gill, H.S., et al., "Pocketed microneedles for drug delivery to the skin," Journal of Physics and Chemistry of Solids, vol. 69, 2008, pp. 1537-1541.

Griss, P., et al., "Characterization of Micromachined Spiked Biopotential Electrodes," IEEE Transactions on Biomedical Engineering, vol. 49, No. 6, 2002, pp. 597-604.

Griss, P., et al., "Micromachined Electrodes for Biopotential Measurements," IEEE Journal of MicroElectroMechanical Systems, vol. 10, No. 1, 2001, pp. 10-16.

Haq, M.I., et al., "Clinical administration of microneedles: skin puncture, pain and sensation," Biomed Microdevices, vol. 11, No. 1, 2009, pp. 35-47.

Hines, A.E., et al., "Stimulus artifact removal in EMG from muscles adjacent to stimulated muscles," Journal of Neuroscience Methods, vol. 64, No. 1, 1996, pp. 55-62.

Jobst, G., et al., "Thin-Film Micro-Biosensors for Glucose-Lactate Monitoring," Analytical Chemistry 68, 1996, pp. 3173-3179.

Joseph, L., et al., "High Frequency Stimulation Selectively Blocks Different Types of Fibers in Frog Sciatic Nerve," IEEE Trans. on Neural Systems and Rehabil Eng., vol. 19, No. 5, 2011, pp. 550-557.

Kaushik, S., et al., "Lack of Pain Associated with Microfabricated Microneedles," Anesth Analg, vol. 92, 2001, pp. 502-504.

Keller, O.C., et al. "Voltammetric and Reference Microelectrodes with Integrated Microchannels for Flow-Through Microvoltammetry. 2. Coupling the Microcell to a Supported Liquid Membrane Preconcentration Technique," Analytic Chemistry, vol. 72, 2000, pp. 943-948.

Kilgore, K.L., et al., "Nerve conduction block utilising high-frequency alternating current," Med. Biol. Eng. Comput., vol. 42, No. 3, 2004, pp. 394-406.

Knaflitz, M., et al., "Suppression of Simulation Artifacts from Myoelectric-Evoked Potential Recordings," IEEE Transactions on Biomedical Engineering, vol. 35, vol. 9, 1988, pp. 758-763.

Laurent, A., et al., "Echographic measurement of skin thickness in adults by high frequency ultrasound to assess the appropriate microneedle length for intradermal delivery of vaccines," Vaccine, vol. 25, 2007, pp. 6423-6430.

Lin, C.T., et al., "Noninvasive Neural Prostheses using Mobile and Wireless EEG," Proceedings of the IEEE, vol. 96, No. 7, 2008, pp. 1167-1183.

Martinez, A.W., et al., "Microfabrication and nanotechnology in stent design," WIREs Nanomedicine and Nanobiotechnology, vol. 3, 2011, pp. 256-268.

Matsumoto, T., et al., "Development of a micro-planar Ag/AgCl quasi-reference electrode with long-term stability for an amperometric glucose sensor," Analytica Chimica Acta, vol. 462, 2002, pp. 253-259.

Maurizio, I., et al., "Artifact Removal on surface EMG." Anno Accademico CCLXXIX, vol. XCIV, 2006, 9 pages.

McGill, K.C., et al., "On the Nature and Elimination of Stimulus Artifact in Nerve Signals Evoked and Recorded Using Surface Electrodes," IEEE Transactions on Biomedical Engineering, vol. BME-29, No. 2, 1982, pp. 129-137.

Merletti, R., et al., "Electrically Evoked Myoelectric Signals," Critical Reviews in Biomedical Engineering, vol. 19, No. 4, 1992, pp. 293-340.

Merletti, R., et al., "The linear electrode array: a useful tool with many applications," Journal of Electromyography and Kinesiology, vol. 13, No. 1, 2003, pp. 37-47.

Mezzi, A., et al., "Micro-chemical surface investigation of brittle carthaginian and roman silver artefacts," Surface and Interface Analysis, vol. 44, 2012, pp. 972-976.

Mikszta, J.A., et al., "Improved genetic immunization via micromechanical disruption of skin-barrier function and targeted epidermal delivery," Nature Medicine, vol. 8, 2002, pp. 415-419.

Minzly, J., et al., "Stimulus artefact suppressor for EMG recording during FES by a constant-current stimulator," Medical & Biological Engineering & Computing, vol. 31, No. 1, 1993, pp. 72-75.

Nam, Y., et al., "A retrofitted neural recording system with a novel stimulation IC to monitor early neural responses from a stimulating electrode," Journal of Neuroscience Methods, vol. 178, No. 1, 2009, pp. 99-102.

Norman, J.J., et al., "Hollow microneedles for intradermal injection fabricated by sacrificial micromolding and selective electrodeposition," Biomed Microdevices, vol. 15, Apr. 2013, pp. 203-210.

(56) References Cited

OTHER PUBLICATIONS

O'Keeffe, D.T., et al., "Stimulus artifact removal using a software-based two-stage peak detection algorithm," Journal of Neuroscience Methods, vol. 109, No. 2, 2001, pp. 137-145.

Ortiz-Catalan, M., et al., "On the viability of implantable electrodes for natural control of artificial limbs: Review and discussion," BioMedical Engineering OnLine, vol. 11, No. 33, 2012, 24 pages.

Park, E.S., et al., "Measurement of Median Sensory Nerve Conduction Velocity in Koreans, using Somatosensory Evoked Potential," Yonsei Medical Journal, vol. 27, No. 3, 1986, pp. 227-233.

Park, J.I., "Preoperative Percutaneous Cranial Nerve Mapping in Head and Neck Surgery," Arch Facial Plast Surg., vol. 5, 2003, pp. 86-91.

Park, J-H., et al., "Tapered Conical Polymer Microneedles Fabricated using an Integrated Lens Technique for Transdermal Drug Delivery," IEEE Transactions on Biomedical Engineering, vol. 54, No. 5, 2007, pp. 903-913.

Peckham, P.H., et al., "Functional Electrical Stimulation for Neuromuscular Applications," Annual Review of Biomedical Engineering, vol. 7, 2005, pp. 327-360.

Polk, B.J., et al., "Ag/AgCl microelectrodes with improved stability for microfluidics," Sensors and Actuators B, vol. 114, 2006, pp. 239-247.

Prausnitz, M.R., "Microneedles for transdermal drug delivery," Advanced Drug Delivery Reviews, vol. 56, 2004, pp. 581-587.

Scott, R.N., et al., "Stimulus artefact in somatosensory evoked potential measurement," Medical and Biological Engineering and Computing, vol. 35, No. 3, 1997, pp. 211-215.

Searle, A., et al., "A direct comparison of wet, dry and insulating bioelectric recording electrodes," Physiological Measurement, vol. 21, No. 2, 2000, pp. 271-283.

Seror, P. "Comparative Diagnostic Sensitivities of Orthodromic or Antidromic Sensory Inching Test in Mild Carpal Tunnel Syndrome," Archives of Physical Medicine Rehabilitation, vol. 81, No. 4, 2000, pp. 442-446.

Tai, C., et al., "Bladder Inhibition by Intermittent Pudendal Nerve Stimulation in Cat Using Transdermal Amplitude Modulated Signal (TAMS)," Neurourology and Urodynamics, vol. 31, 2012, pp. 1181-1184.

Tanner, J.A., "Reversible Blocking of Nerve Conduction by Alternating Current Excitation." Nature, vol. 195, 1962, pp. 712-713.

Thorsen, R., "An Artefact Suppressing Fast-Recovery Myoelectric Amplifier," IEEE Transactions on Biomedical Engineering, vol. 46, No. 6, 1999, pp. 764-766.

Wagenaar, D.A., et al., "Real-time multi-channel stimulus artifact suppression by local curve fitting," Journal of Neuroscience Methods, vol. 120, No. 2, 2002, pp. 113-120.

Wermeling, D.P., et al., "Microneedles permit transdermal delivery of a skin-impermeant medication to humans," Proc. of the National Academy of Sciences, vol. 105, No. 6, 2008, pp. 2058-2063.

Wichmann, T., "A digital averaging method for removal of stimulus artifacts in neurophysiologic experiments," Journal of Neuroscience Methods, vol. 98, No. 1, 2000, pp. 57-62.

Zhao, H., et al., "Electrochemical polishing of 316L stainless steel slotted tube coronary stents," Journal of Materials Science: Materials in Medicine, vol. 13, 2002, pp. 911-916.

Zwarts, M.J., et al., "Multichannel Surface EMG: Basic Aspects and Clinical Utility," Muscle Nerve, vol. 28, No. 1, 2003, pp. 1-17.

\* cited by examiner

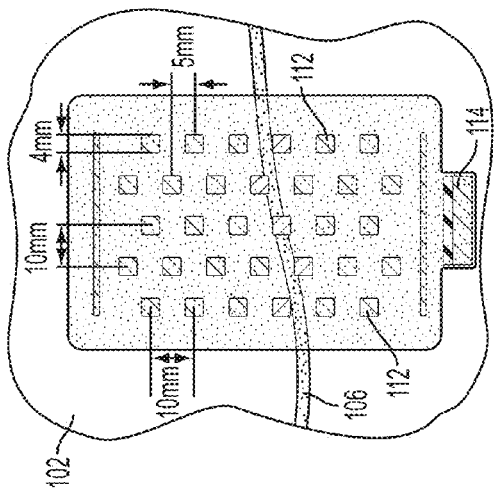
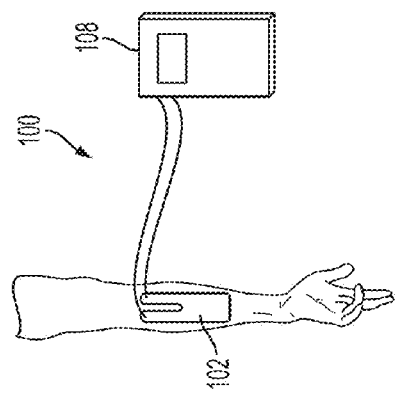
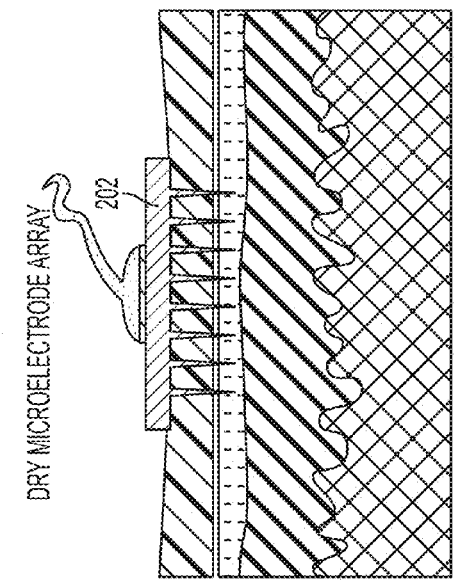
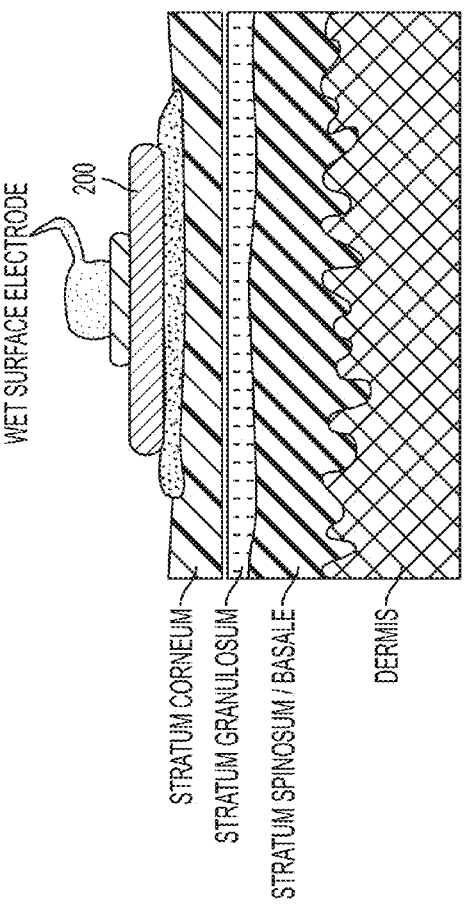

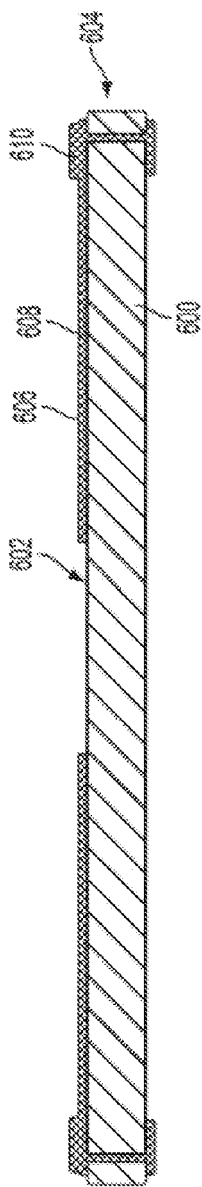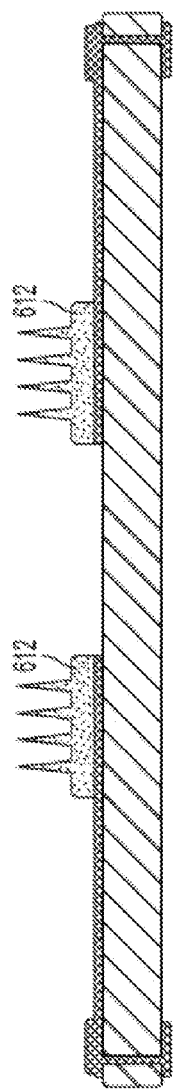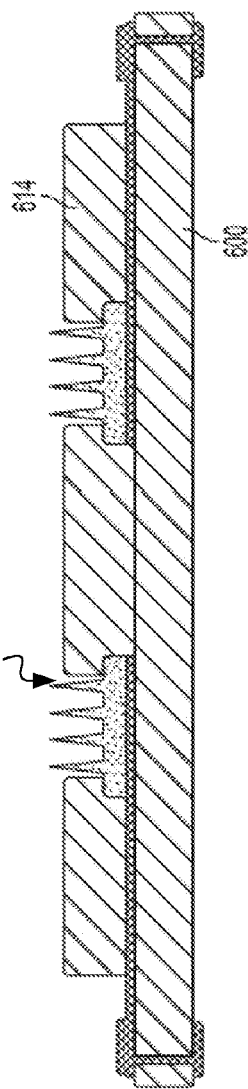

NON-INVASIVE SEGMENTABLE THREE-DIMENSIONAL MICROELECTRODE ARRAY PATCH FOR NEUROPHYSIOLOGICAL DIAGNOSTICS AND THERAPEUTIC STIMULATION

CROSS-REFERENCE TO RELATED APPLICATIONS

This application claims priority to and the benefit of U.S. Provisional Application Ser. No. 61/773,237, filed on Mar. 6, 2013, entitled "A Non-Invasive Segmentable Three-Dimensional Microelectrode Array Patch for Neurophysiological Diagnostics and Therapeutic Stimulation," which application is hereby incorporated in its entirety in this document by reference.

STATEMENT REGARDING FEDERALLY SPONSORED RESEARCH OR DEVELOPMENT

This invention was made with Government support under grant number 1 R43 NS065545-01A1, awarded by the National Institutes of Health. The Government has certain rights in the invention.

BACKGROUND

The Field of the Invention

Implementations described herein relate generally to microneedle electrode patches and, more particularly, to microneedle electrode patches comprising a microneedle electrode array where each of the microneedle electrodes are individually addressable via an external electronics assembly, as well as systems and methods thereof.

Related Art

Traditional nerve conduction studies are typically performed by placing two sets of large area surface electrodes on the skin overlying a nerve, one for recording and one for stimulation. In the case of motor studies, the recording electrodes are typically placed over a muscle innervated by the nerve rather than the nerve itself. Current pulses are then passed through the stimulating electrodes, leading to depolarization of underlying nerves. This depolarization propagates along the nerve in both directions. When the wave of depolarization passes through the tissue underlying the recording electrodes, the electrode records a generated voltage that then analyzed. The two measurements commonly used in traditional nerve conduction studies are the response amplitude and the conduction velocity. The response amplitude is typically reduced in cases of axonal loss. The conduction velocity is typically reduced in demyelinating disease.

Despite operator effort to place the stimulating and recording electrodes as close to the course of the target nerve as possible, anatomic variability can cause unavoidable errors in electrode positioning. With regard to the stimulating electrodes, positioning errors can cause an increase in the electrical current required to deliver an adequate stimulus to the nerve under test, leading to patient discomfort and unintentional stimulation of adjacent nerves. With regard to recording electrodes, positioning errors can cause artifacts such as baseline deflections and reduction in maximal amplitude. In clinical practice, placement errors can be minimized by using stimulus and recording sites having minimal anatomic variability and ensuring the test is conducted by a trained operator capable of recognizing placement error artifacts and adjusting electrode positions to minimize them.

An ideal set of surface stimulating electrodes should be very small and located directly over the nerve of interest, thereby delivering maximum current to the target while minimizing unintentional stimulation of the surrounding tissue. Likewise, ideal recording electrodes would be very small and located directly over the nerve of interest, thereby maximizing the signal recorded from the target while minimizing artifact produced by surrounding tissue.

Simply increasing electrode size, thereby increasing the chance that the nerve lays directly underneath some portion of the electrode, is not an effective mechanism for reducing placement error. In the case of stimulating electrodes, larger active sites typically require larger current pulses to depolarize an underlying nerve and, thus, increase unintentional stimulation of nearby tissue. In the case of recording electrodes, a larger active site does typically reduce the distance between an underlying nerve and the electrode pad, thereby increasing the signal produced by that nerve's depolarization; however, it also increases the volume of unrelated tissue lying under the pad, which will increase the recorded noise and artifact.

Conventional nerve conduction studies have typically been limited by the presence of stimulation artifacts that obscure evoked nerve and muscle signals. In practice, such stimulation artifacts can be minimized by increasing the distance between the stimulation and recording electrodes, allowing the stimulus artifact to dissipate before the evoked potential reaches the recording site. While effective, increasing the distance between the stimulation and recording electrodes makes it difficult to assess peripheral nerves over comparably short lengths and potentially reduces sensitivity. For example, a short region of conduction velocity slowing (e.g., the median nerve at the wrist, as in carpal tunnel syndrome) can be clearly seen when the stimulus and recording electrodes lie directly on either side of that region; however, if the electrodes are separated from that region by a long length of normal nerve, the net observed conduction velocity can be normal despite the disease state. Accordingly, ideal stimulating and recording electrodes should incorporate a mechanism for preventing or removing stimulation artifact, allowing stimulation and recording to occur at very close proximity to each other and enabling a wider variety of focal nerve assessment.

Accordingly, a need exists for improved devices, systems and methods for performing nerve conduction studies and related measurements.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

Implementations of the present invention provide for microneedle electrode patches comprising a first flexible substrate, at least one microneedle electrode array, and a second flexible substrate. In some aspects, a first flexible substrate can have a surface, a lateral edge and at least one conductive pad disposed on the surface and having a conductive trace extending from the conductive pad proximate to the lateral edge of the first flexible substrate. In some aspects, at least one microneedle electrode array can be formed from a conductive substrate having a plurality of microneedles extending from at least an upper surface thereof and a lower surface adapted to contact a corresponding one of the at least one conductive pad on the first substrate. In some aspects, the microneedle electrode array can further comprise a coating. In some aspects, the second flexible substrate can have at least one opening defined therein dimensioned to accommodate at least the portion of the upper surface of one of the at least one microneedle electrode array from which the plurality of microneedles extend. It is contemplated that the at least one conductive pad and the at least one microneedle electrode array are disposed in electrical communication and that the first and second substrates are bonded together.

Implementations of the present disclosure also provide for a microneedle electrode system comprising a microneedle electrode patch, an external electronics assembly connected to the electrical contact of each of the plurality of microneedle electrode arrays, wherein the external electronics can be adapted to at least one of stimulate and record electrical activity of each microneedle electrode array. It is further contemplated that each of the microneedle electrode arrays can be individually-addressable and that, in operation, the microneedle electrode arrays are adapted to be selectively functionally integrated via the external electronics assembly to form an effective electrode.

Implementations of the present disclosure further provide for a methods for using a microneedle electrode system comprising the steps of providing a microneedle electrode system, applying the patch to a target region comprising at least one nerve, selectively stimulating a first portion of the plurality of microneedle electrode arrays, and selectively recording the evoked electrical activity from a second portion of the plurality of microneedle electrode arrays.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate several aspects described below and together with the description, serve to explain the principles of the invention. Like numbers represent the same elements throughout the figures. The patent or application file contains at least one drawing executed in color. Copies of this patent or patent application publication with color drawing(s) will be provided by the Office upon request and the payment of the necessary fee.

FIG. 1A shows a schematic of a microneedle electrode system of the present disclosure in use. FIG. 1B shows a top view of a microneedle electrode patch of the present disclosure.

FIG. 2A shows a schematic of a large-area surface electrode in use. FIG. 2B shows a schematic of a microneedle electrode array of the present disclosure in use.

FIG. 3A shows planar batch fabricated microneedle electrode arrays. FIG. 3B shows microneedle electrode arrays converted from a planar configuration to a three-dimensional configuration. FIG. 3C shows a low-impedance coating deposited on the microneedle electrode arrays.

FIGS. 6A-6C illustrate a side view of one exemplary fabrication sequence of a microneedle electrode patch. FIG. 6A shows a conductive pads and conductive traces on a first flexible substrate. FIG. 6B shows a plurality of microneedle electrode arrays disposed on the conductive pads of the first flexible substrate. FIG. 6C shows a second flexible substrate bonded to the first flexible substrate and having openings defined therein to accommodate the plurality of microneedle electrode arrays.

FIG. 10A shows the raw signal propagation from a radial sensory nerve across the microneedle electrode array patch. Shaded gray bars indicate the duration of artifact elimination applied by the external electronics assembly. FIG. 10B shows corresponding functional nerve images created by showing the signal amplitude from each microneedle electrode array as an interpolated time-lapse image. The panel progression demonstrates propagation of the depolarization (red) and hyperpolarization (blue) across the patch in time.

DETAILED DESCRIPTION

Figure 3A:
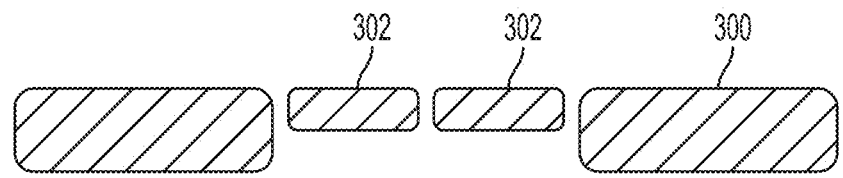
FIGS. 3A-3C illustrates a side view of one exemplary microfabrication sequence for microneedle electrode arrays of the present invention.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well known aspects of nerve conduction studies and microfabrication techniques have not been described in particular detail in order to avoid unnecessarily obscuring aspects of the disclosed implementations.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be perdefined it is understood that each of these additional steps can be perdefined with any specific aspect or combination of aspects of the disclosed methods.

Implementations described herein are directed towards devices, systems and methods adapted to deliver electrical stimuli to muscles and/or nerves and subsequently record the electrical signals elicited by the initial stimuli at at least a second location. In one aspect, a microneedle electrode patch comprises a plurality of individually addressable microneedle electrode arrays, each microneedle electrode array having a plurality of microneedles extending from an upper surface thereof. The microneedle electrode arrays can be dimensioned to penetrate the outermost layer of skin to a desired depth in a minimally-invasive fashion, thereby reducing discomfort experienced by the patient. The microneedle electrode patch can be connected to an external electronics assembly adapted to selectively stimulate or record electrical activity at each of the plurality of microneedle electrode arrays in order to form effective electrodes. In other aspects, methods for using the microneedle electrode patches described herein are provided.

Reference will now be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well known aspects of flooring performance testing have not been described in particular detail in order to avoid unnecessarily obscuring aspects of the disclosed implementations.

Turning now to FIGS. 1A and 1B, an implementation of one exemplary aspect of microneedle electrode system 100 is illustrated. Here, a microneedle electrode patch 102 can be applied to a skin surface overlying at least one of a muscle and/or nerve 106. Each electrode patch 102 can be connected to an external electronics assembly 108 adapted to selectively stimulate and record the electrical response of the muscle and/or nerve 106. A single microneedle electrode patch can comprise a plurality of individually addressable microneedle electrode arrays 112, each having a unique electrical contact 114 and adapted to be selectively controlled by the external electronics assembly 108.

One skilled in the art will appreciate that having a microneedle electrode patch 102 comprising individually addressable microneedle electrode arrays 112 selectively controlled by an external electronics assembly 108 can reduce the degree of operator training required to perform neurodiagnostic studies. Furthermore, such systems can also allow for comparative studies between effective electrodes created in a single microneedle electrode patch 102, making measurement of such parameters as local nerve conduction velocity much more straightforward. In light of the present disclosure, one skilled in the art will also appreciate that such a microneedle electrode system 100 can enable further segmentation of the plurality of microneedle electrode arrays 112 into multiple simultaneously-effective electrodes, allowing electrical potentials to be measured at multiple points along the course of a subcutaneous muscle and/or nerve.

In one aspect, in operation, accurate and repeatable calculations of nerve conduction velocity can thus be achieved by correlating the time delay between the evoked potential measured at different effective electrodes and the distance between those sites. Such calculations are more repeatable than traditional calculations that require an operator to manually measure the distance between two electrodes after the optimal recording locations have been manually determined as these calculations are highly sensitive not only to operator training, but also to changes in nerve course with limb position (e.g., subluxation of the ulnar nerve as the elbow moves from an extended to a flexed position). The direct measurement-enabled microneedle electrode systems 100 disclosed herein can minimize or eliminate these confounding factors.

FIG. 2A depicts a conventional large-area surface electrode 200 in use and FIG. 2B depicts a microneedle electrode array 202 of the present disclosure in use. As compared to conventional large-area surface electrodes 200, the three-dimensional microneedle electrode arrays 202 described herein enable significant improvement in signal fidelity for a dramatic reduction in electrode footprint. In light of the present disclosure, one skilled in the art will appreciate that these three-dimensional microneedle electrode arrays 202 can enable improved signal-to-noise ratio by recording only over the area of interest and can enable a reduction in the total current necessary to deliver an electrical stimulus of given intensity. Notably, while the small size of the individual microneedle electrode arrays 112 might be expected to compromise recorded signal quality when compared to conventional surface electrodes, the use of microneedle electrode array electrodes can enable electrical signals to bypass the outer layers of skin, dramatically reducing the resistance to current and increasing signal fidelity despite the increased spatial resolution.

Figure 3B:
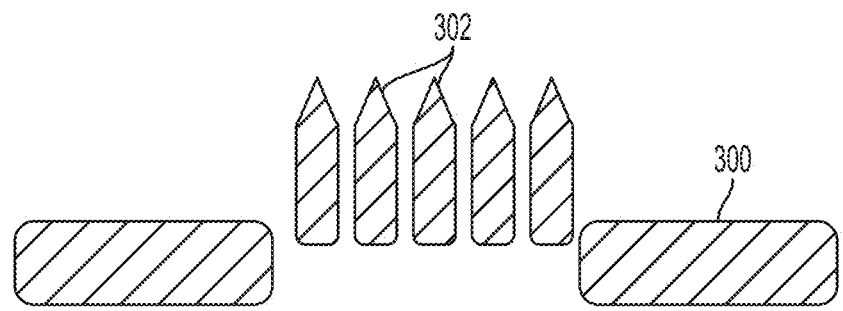
Figure 3C:
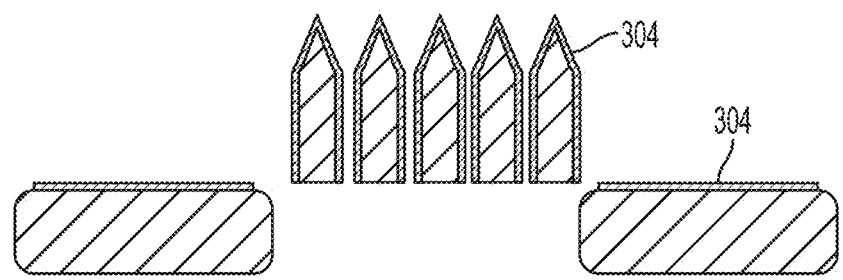
Figure 4B:
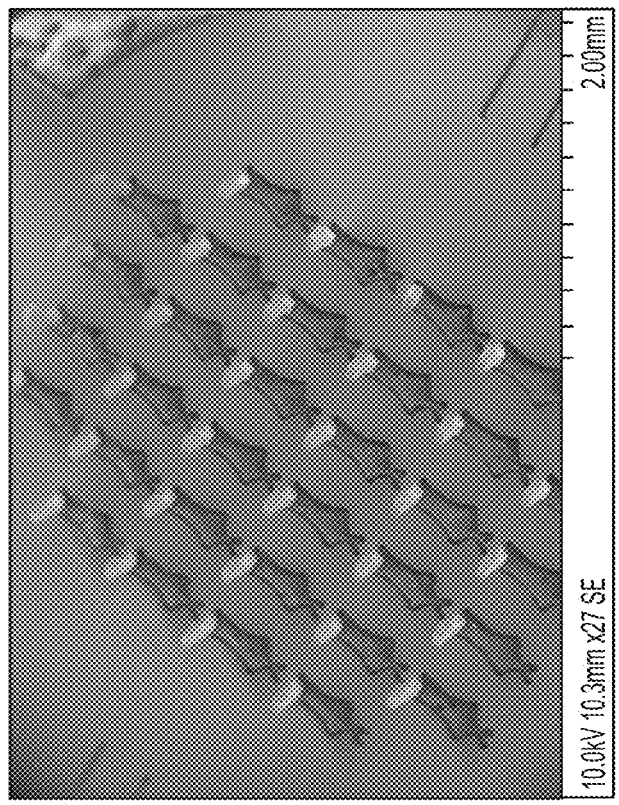
FIG. 4A is a scanning electron micrograph (SEM) showing the microneedle electrode array having a plurality of 2-D microneedles prior to conversion to 3-D and FIG. 4B is a micrograph showing the microneedle electrode array with the plurality of microneedles in a final 3-D orientation.
Figure 4A:
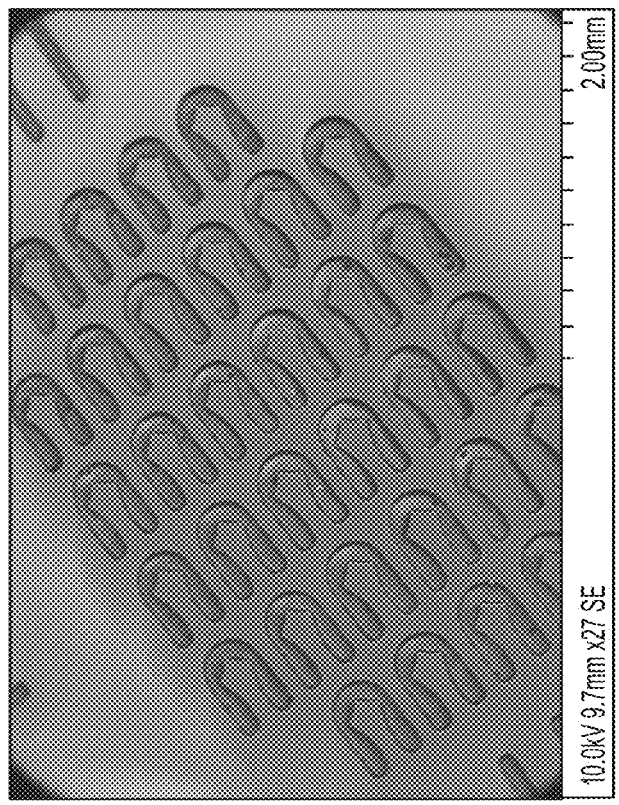
Figure 5A:
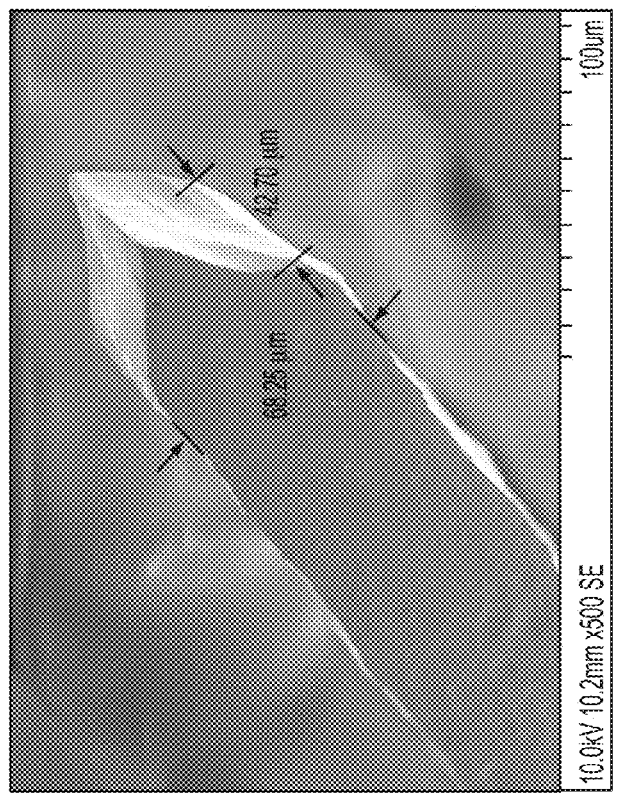
FIG. 5A is an SEM showing a single microneedle having a hooked geometry and FIG. 5B is an SEM showing a single microneedle having a regular geometry.
Figure 5B:
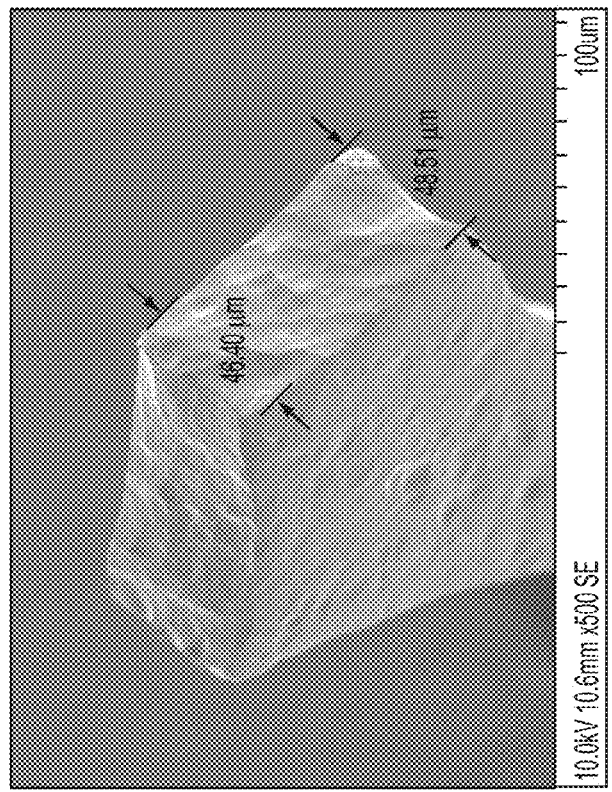

FIGS. 3A, 3B and 3C depict one embodiment of a fabrication sequence to form the microneedle electrode arrays. As shown in FIG. 3A, a stainless steel substrate 300 can be laser machined, or photochemically milled, or mechanically stamped to create individual microneedles 302 in plane with the substrate. The microneedles 302 can be mechanically converted to a three-dimensional configuration by moving them to an out-of-plane configuration as shown in FIG. 3B. (FIGS. 4A and 4B show a micrograph of in-plane microneedles and out-of-plane microneedles, respectively.) Here, the stainless steel substrate 300 can undergo at least one of acid pickling and electropolishing to achieve a desired tip sharpness and geometry. These parameters can be controlled to produce a "hooked" tip as shown in FIG. 5A or a conventional needle tip as shown in FIG. 5B. One skilled in the art will appreciate that the tip geometry needs to be sized and shaped to pierce the stratum corneum of skin. The microneedles 302 can be sized and shaped to pierce the stratum granulosum of skin. Next the surface of the microneedle electrode array can be coated with a metal 304 as shown in FIG. 3C. Metallization of the microneedle electrode arrays with low-impedance coatings can enable lower noise and, correspondingly, higher sensitivity microelectrodes having higher signal fidelity. In one aspect, the metal can be a low-impedance porous material and, in a further aspect, can be selected from the group comprising silver/silver chloride, titanium/platinum, nanoporous platinum, PEDOT:PSS, polyaniline, titanium nitride, and indium tin oxide. In one illustrative example, stainless steel microneedle electrode arrays can be coated with a layer of silver/silver chloride using sputter deposition in a high-vacuum environment followed by wet/dry plasma functionalization as is known in the art. In other aspects, the coatings can be applied via, for example, electrodeposition, electroplating, thin film deposition, sputter deposition; e-beam deposition; physical vapor deposition and like techniques or any combination thereof. In another aspect, the microneedles comprising the microneedle electrode array can have a height of from about 100 to about 1000 µm above the upper surface of the microneedle electrode array.

Figure 9:
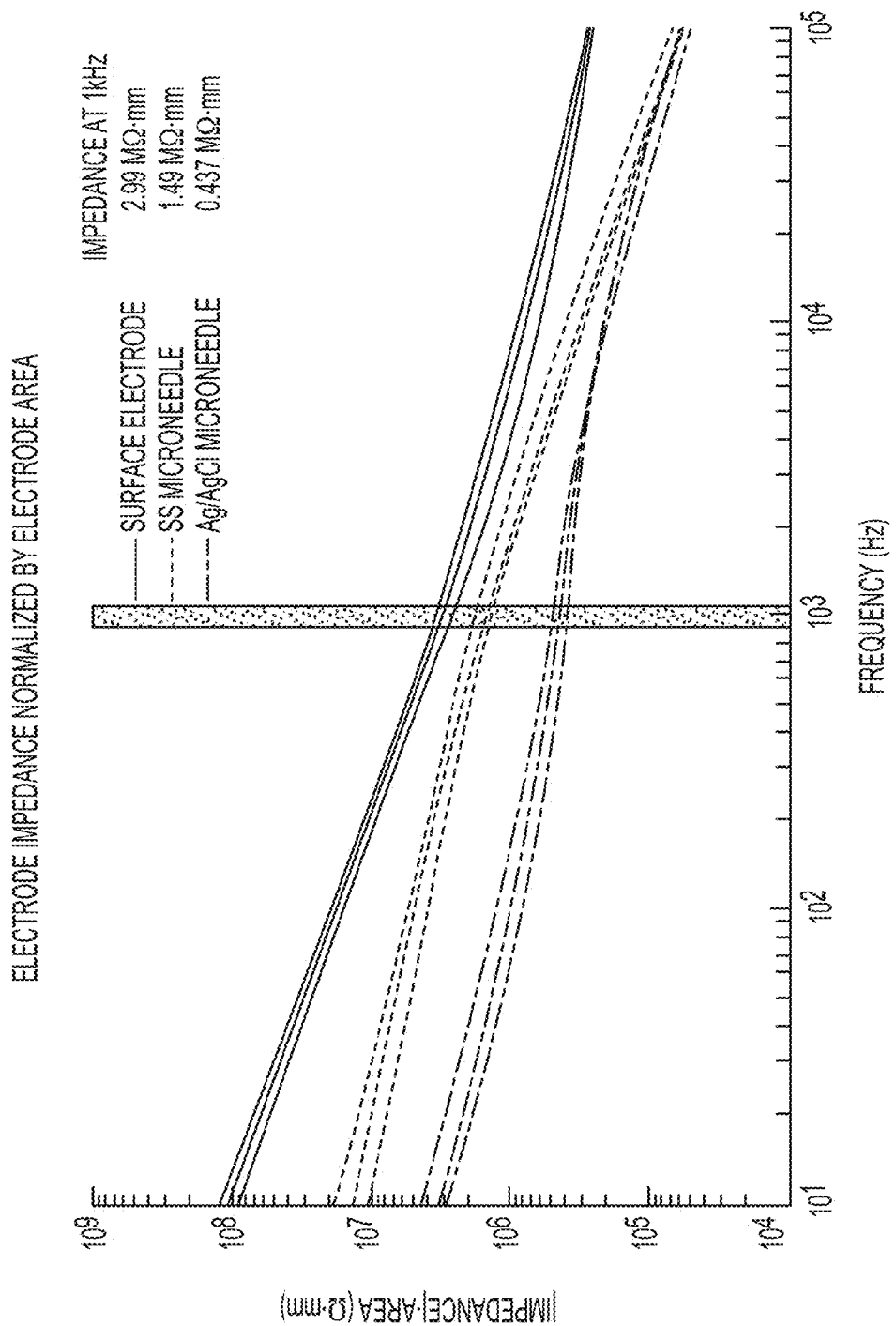
FIG. 9 is a graph illustrating the electrode impedance normalized by electrode area and provides an impedance spectroscopy comparison between standard electrodes (surface) and microneedle electrode arrays.

A graph illustrating the electrode impedance normalized by electrode area and provides an impedance spectroscopy comparison between standard electrodes (surface) and microneedle electrode arrays is shown in FIG. 9. Microneedle electrode arrays of the present disclosure show nearly an order of magnitude impedance reduction for an area that is 25× smaller. One skilled in the art will appreciate that such impedance and size reduction result in improved signal fidelity in nerve-conduction study (NCS) applications.

In an alternate aspect, the microneedle electrode arrays can be fabricated from polymer substrates such as, for example and without limitation, polymethylmethacrylate, polyurethane, SU-8, polylactic acid, polylactic-co-glycolic acid, polyethylene glycol, Kapton and the like utilizing techniques such as micromolding, three-dimensional lithography and double-side exposure of photodefinable materials. The sharpness of these polymer substrates can be controlled to achieve a target tip diameter utilizing reactive ion etching (RIE) techniques.

In another alternate aspect, thin film metal can be transferred from a micromold to a microneedle structure during the process of molding to allow for simultaneous formation of microneedle structures and functionally coating the structures with a conductive layer as detailed in U.S. Patent Publication No. 2008/0063866, published Mar. 13, 2008, which is hereby incorporated by reference in its entirety.

FIGS. 6A-6C illustrate a side view of one exemplary fabrication sequence of a microneedle electrode patch. FIG. 6A illustrates a first flexible substrate 600 having a surface 602, a lateral edge 604, and a plurality of conductive pads 606 disposed thereon. The first flexible substrate 600 can be fabricated from a polymer substrate such as, for example, Kapton. In one aspect, each conductive pad further comprises a conductive trace 608 extending therefrom and terminating proximate a lateral edge of the first flexible substrate at an electrical contact 610. FIG. 6B shows a plurality of microneedle electrode arrays 612 disposed on a corresponding one of the plurality of conductive pads 606 on the first substrate 600. FIG. 6C shows a second flexible substrate 614 having a plurality of openings 616 defined therein dimensioned to accommodate at least the portion of the upper surface of the microneedle electrode array 612 from which the plurality of microneedles extend. Here, the plurality of conductive pads and the plurality of microneedle electrode arrays are disposed in electrical communication and the first and second substrates are bonded together forming a microneedle electrode patch. The second flexible substrate 614 can be fabricated from a polymer substrate such as, for example, Kapton.

Figure 7A:
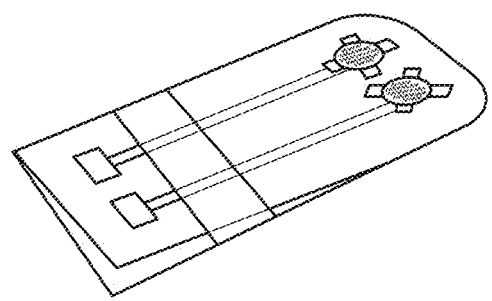
FIG. 7A shows one example of a microneedle electrode patch having two electrodes.
Figure 7B:
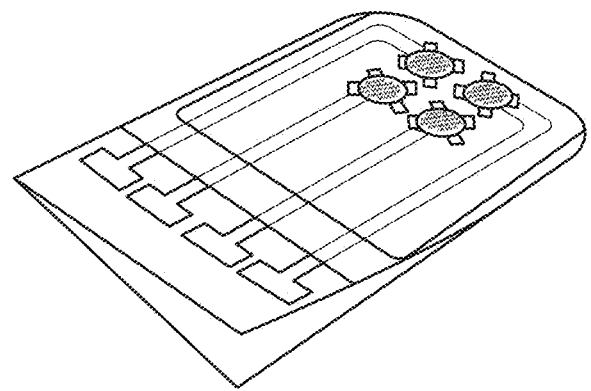
FIG. 7B shows one example of a microneedle electrode patch having four electrodes.
Figure 8:
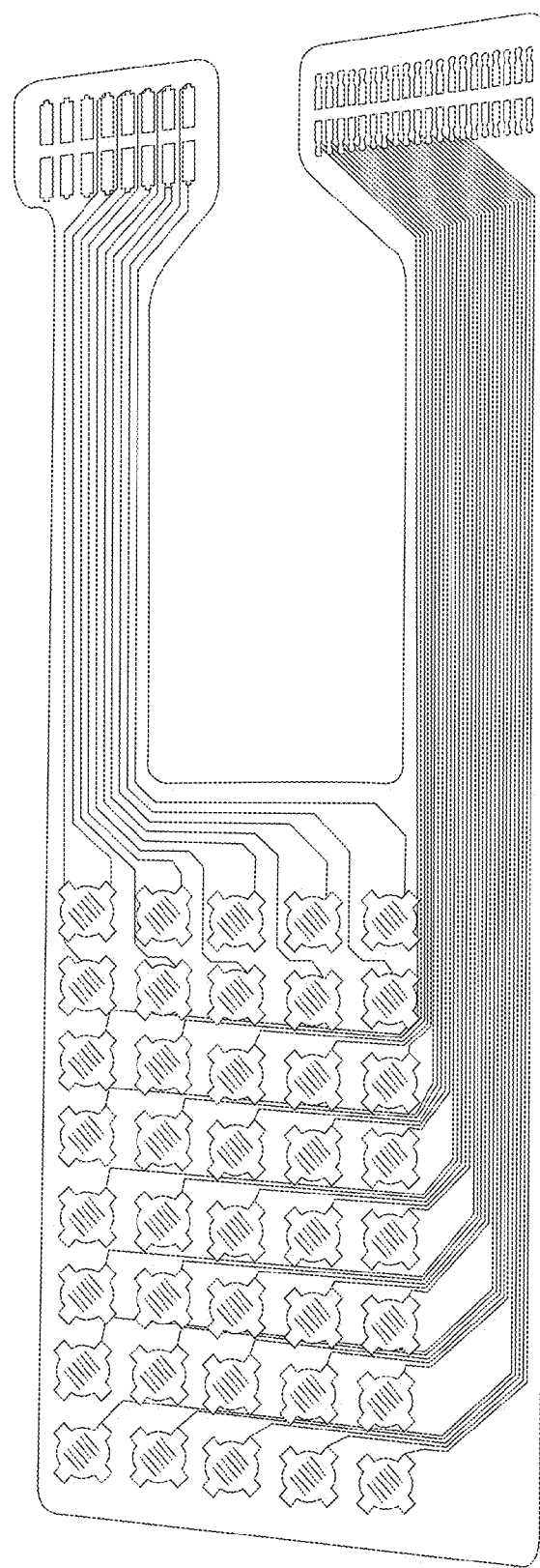
FIG. 8 shows one example of a microneedle electrode patch having 40 individually addressable microneedle electrodes.

A microneedle electrode patch having two microneedle electrode arrays is depicted in FIG. 7A and having four microneedle electrode arrays is depicted in FIG. 7B. FIG. 8 illustrates a microneedle electrode patch having 40 microneedle electrode arrays.

In light of the present disclosure, one skilled in the art will appreciate that the disclosed fabrication techniques can produce microneedle electrode arrays that have low impedance characteristics while also presenting a much smaller surface area than conventional surface electrodes. Without being limited by theory or simulation, this is believed to reduce noise in recorded signals, reduce the amount of voltage required to deliver an effective stimulus current, and allow higher spatial resolution when the microneedle electrode arrays are patterned on an electrode patch.

Figure 10A:
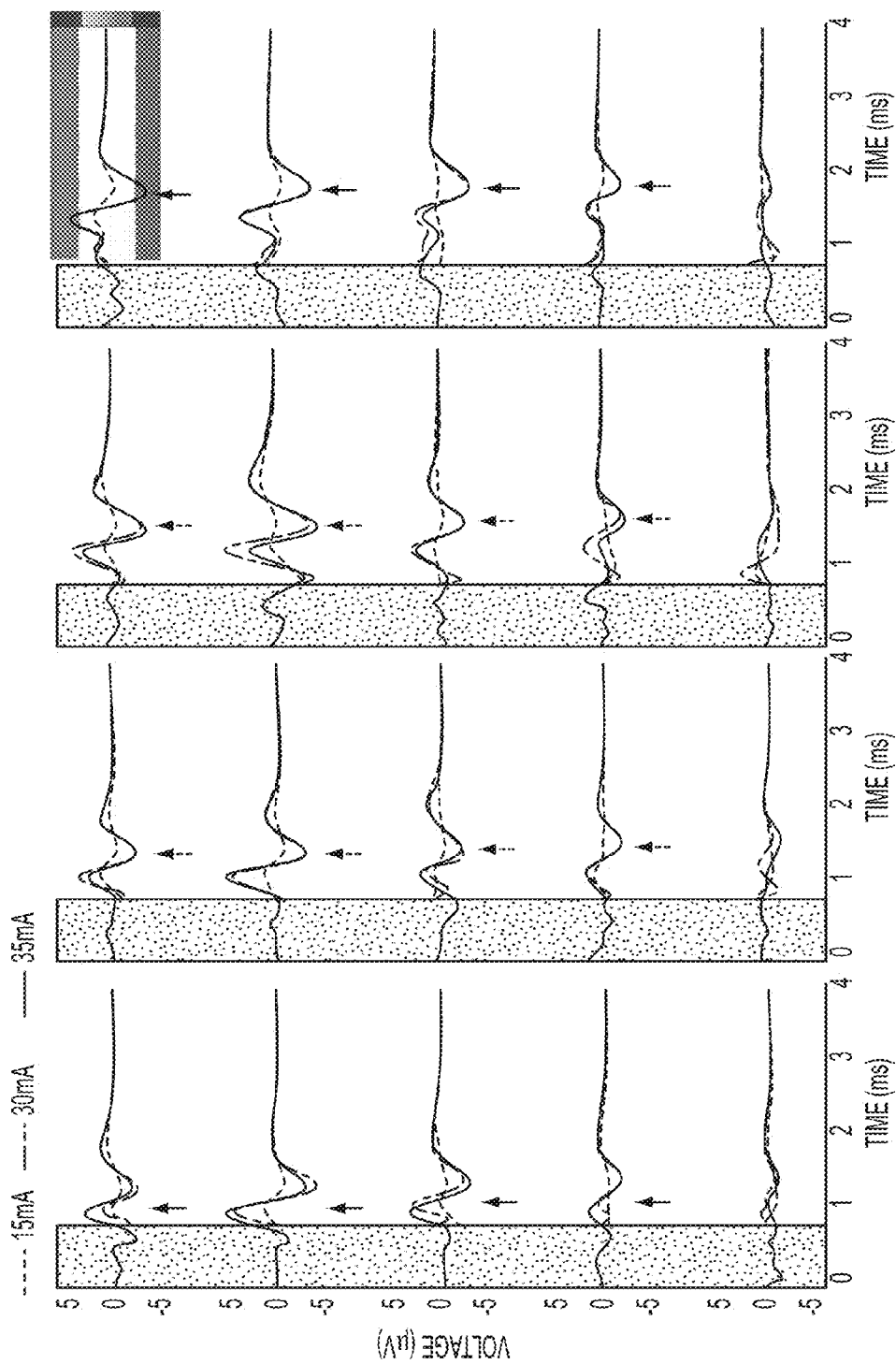
FIGS. 10A and 10B illustrate an exemplary aspect of a functional nerve assessment from a test subject.
Figure 10B:
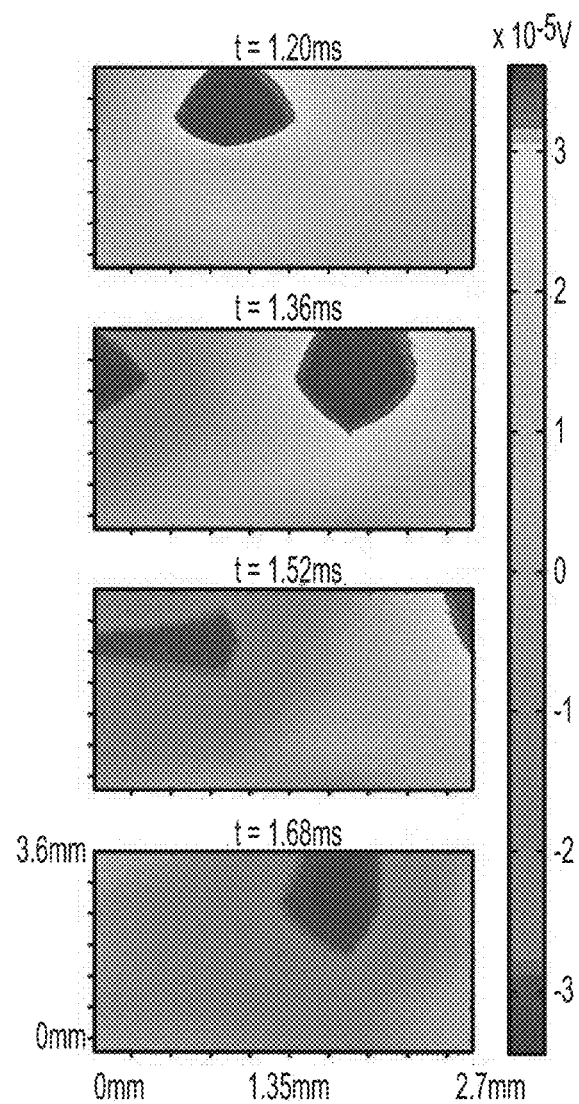
Figure 11:
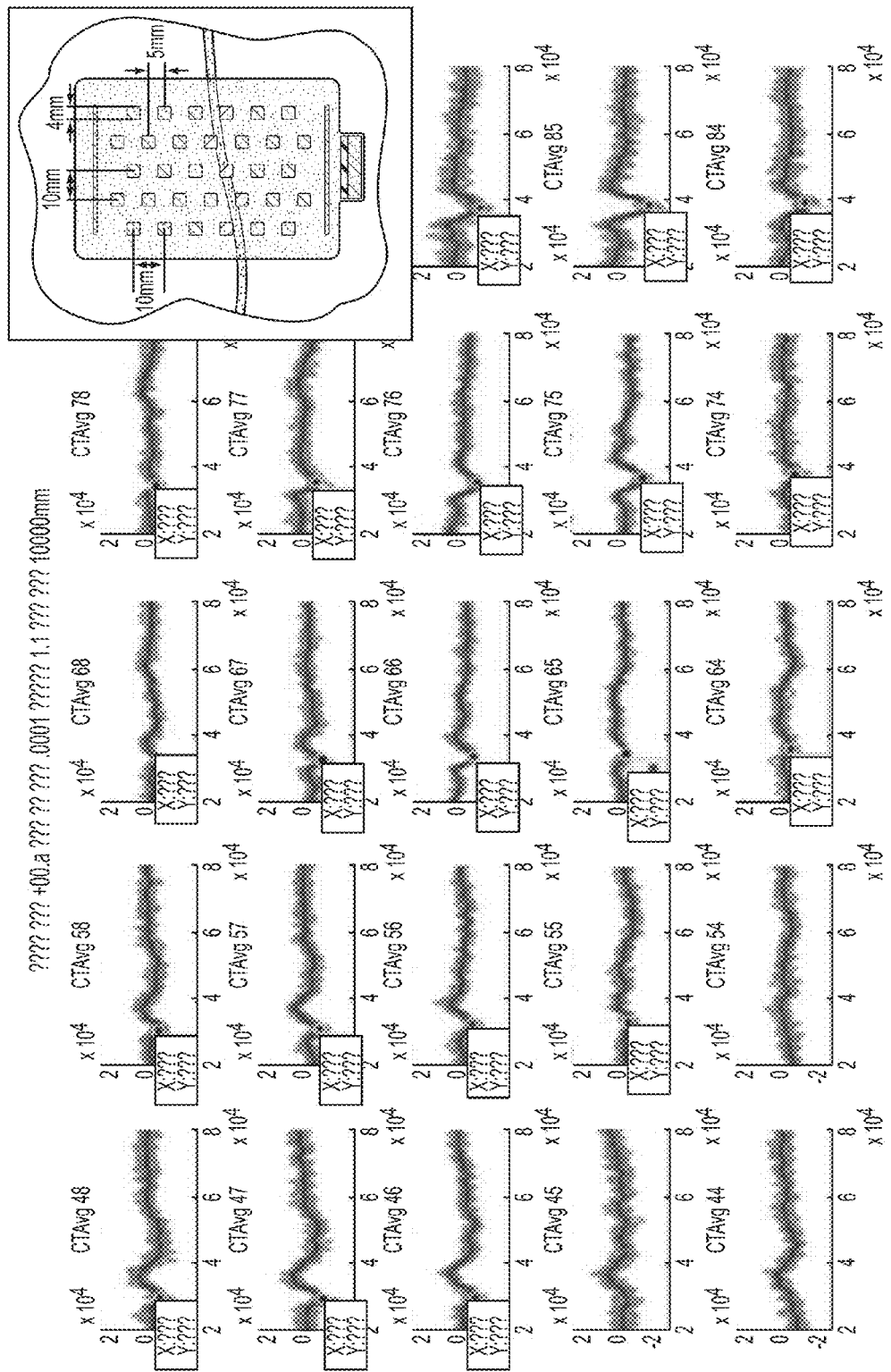

In one aspect and as shown in FIGS. 10A and 10B, an array of plots resulting from individually recording each one of an array of microneedle electrodes integrated into a single microneedle electrode patch enables nerve-mapping. Each plot represents a recording from each of the micro-needle electrode arrays on a microneedle electrode patch applied to the skin. Each plot depicts pulses from the median-nerve. In a further aspect, and as shown in the inset, the microneedle electrode system can also algorithmically determine and display the course and speed of the underlying nerve based on the information recorded at each microneedle electrode array.

In other aspects, the present disclosure provides for methods for using the microneedle electrode systems provided herein for expediting traditional nerve conduction studies. In one aspect, the course of subcutaneous nerves can be algorithmically determined and, by using only those active sites closest to the nerve under test, the system can enable a relatively untrained operator to achieve ideal electrode placement despite anatomic variations. This can improve the validity of nerve conduction studies and can improve test-to-test repeatability, increasing the ability of the system to monitor disease progress over time. In other aspects, the systems and methods provided herein can allow a single microneedle electrode array to perform both stimulation and recording, removing the need for separate electrodes in some cases. In a further aspect, nerve conduction studies that require measurement at multiple locations along the same nerve (e.g., inching studies in carpal tunnel syndrome) can be performed using a single stimulus with multiple simultaneous recording sites as opposed to repeated stimuli as a single recording electrode is carefully moved along the nerve course, both expediting the exam and reducing demands upon the operator. In other aspects, using differential stimulation patterns (e.g., long duration low current vs. short duration high current), the sensory or motor fibers of a given nerve can be preferentially stimulated. This enables the sensory and motor components of a mixed nerve to be assessed without moving the recording sites.

In other aspects, the present disclosure provides for systems and methods where a stimulus can be delivered to a distant site through either a conventional surface electrode or a second array. In light of the present disclosure, one skilled in the art will appreciate that this can enable indirect assessment of the intervening nerve length as well as assessment of the portion of nerve underlying the array itself. In yet other aspects, differential stimulation techniques can be used to selectively stimulate sensory or motor nerve fibers in the same mixed peripheral nerve, enabling assessment of both fiber types without moving the patch and/or stimulus locations.

In other aspects, the present disclosure provides for methods for using the disclosed system for therapeutic stimulation. In one exemplary aspect, the electrode array can be used to monitor the evoked response to therapeutic stimulation, allowing stimulation intensity to be modulated to maintain a fixed response level. In other aspects, in paroxysmal disorders, such as migraine or occipital neuralgia, the system can be used to monitor for changes in local nerve parameters that suggest an impending event, and then either alert the patient or automatically trigger a therapeutic stimulus.

In other aspects, the present disclosure provides methods for using the disclosed system for home monitoring of neurophysiological parameters. In one exemplary aspect, the ability to optimize stimulation location of the system without user intervention raises the possibility of a patient performing simple neurophysiological testing at home, in the same way that diabetics monitor their blood sugar. It is contemplated that a patient with a known peripheral nerve disease could place an array patch over an affected nerve, at which point the external electronics assembly would locate the nerve, stimulate the nerve at one end, and record the evoked response along the nerve length. By allowing rapid calculation of response amplitude and conduction velocity with minimal user intervention, such a device could indicate that a chronic neuropathy (e.g., chronic inflammatory demyelinating polyneuropathy or CIDP) is objectively worsening, and that a change in treatment regimen is required to prevent further clinical deterioration and/or hospitalization.

What is claimed is:

1. A microneedle electrode patch, comprising:
    a first flexible substrate having a surface, a lateral edge and at least one conductive pad, wherein a corresponding at least one conductive trace extends from the at least one conductive pad disposed on the surface proximate the lateral edge of the first flexible substrate,
    at least one microneedle electrode array formed from a conductive substrate having a plurality of microneedles extending from at least a portion of an upper surface thereof and a lower surface disposed in contact with a corresponding one of the at least one conductive pad on the first flexible substrate, wherein the at least one microneedle electrode array further comprises a coating, and
    a second flexible substrate having at least one opening defined therein dimensioned to accommodate at least the portion of the upper surface of the at least one microneedle electrode array from which the plurality of microneedles extend;
    wherein the at least one conductive pad and the at least one microneedle electrode array are disposed in electrical communication and the first flexible substrate and the second flexible substrate are bonded together, and wherein the plurality of microneedles are sized and shaped to pierce the stratum granulosum of the mammalian skin.

2. The microneedle electrode patch of claim 1, wherein the surface of the first flexible substrate further comprises an upper surface.

3. The microneedle electrode patch of claim 1, wherein the at least one conductive pad and the at least one microneedle electrode array are further disposed in low-impedance electrical communication.

4. The microneedle electrode patch of claim 1, wherein the at least one conductive trace extends laterally from the at least one conductive pad.

5. The microneedle electrode patch of claim 1, wherein the first flexible substrate comprises a polymer.

6. The microneedle electrode patch of claim 5, wherein the second flexible substrate comprises a polymer.

7. The microneedle electrode patch of claim 1, wherein the conductive substrate is at least partially formed from the group consisting of a metal and a polymer.

8. The microneedle electrode patch of claim 7, wherein the metal is stainless steel.

9. The microneedle electrode patch of claim 7, wherein the polymer is selected from the group consisting of poly methyl methacrylate, polyurethane, SU-8, polylactic acid, polylactic-co-glycolic acid, and polyethylene glycol.

10. The microneedle electrode patch of claim 1, wherein the coating is a metal.

11. The microneedle electrode patch of claim 1, wherein the coating is a low-impedance porous material.

12. The microneedle electrode patch of claim 11, wherein the low-impedance porous material is selected from the group consisting of Ag/AgCl, nanoporous Pt, PEDOT:PSS, polyaniline, titanium nitride, and indium tin oxide.

13. The microneedle electrode patch of claim 1, where the at least one microneedle electrode array comprises a plurality of microneedle electrode arrays, wherein each of the plurality of microneedles electrode arrays have an area from about 0.5 to about 75 $mm^2$.

14. The microneedle electrode patch of claim 1, wherein the microneedle electrode patch has an area of from about 500 to about 10000 $mm^2$.

15. The microneedle electrode patch of claim 14, wherein the at least one microneedle electrode array comprises from about 2 to about 20,000 microneedle electrode arrays.

16. The microneedle electrode patch of claim 15, wherein the at least one microneedle electrode array comprises from about 10 to about 1000 microneedle electrode arrays.

17. The microneedle electrode patch of claim 15, wherein the at least one microneedle electrode array comprises from about 2 to about 50 microneedle electrode arrays.

18. A microneedle electrode patch, comprising:
a first flexible substrate having a surface, a lateral edge and at least one conductive pad, wherein a corresponding at least one conductive trace extends from the at least one conductive pad disposed on the surface proximate the lateral edge of the first flexible substrate,
at least one microneedle electrode array formed from a conductive substrate having a plurality of microneedles extending from at least a portion of an upper surface thereof and a lower surface disposed in contact with a corresponding one of the at least one conductive pad on the first flexible substrate, wherein the at least one microneedle electrode array further comprises a coating, and
a second flexible substrate having at least one opening defined therein dimensioned to accommodate at least the portion of the upper surface of the at least one, microneedle electrode array from which the plurality of microneedles extend;
wherein the at least one conductive pad and the at least one microneedle electrode array are disposed in electrical communication and the first flexible substrate and the second flexible substrate are bonded together, and wherein the plurality of microneedles have a height of from about 100 to about 1000 micrometers above the upper surface of the at least one microneedle electrode array.

19. The microneedle electrode patch of claim 18, wherein the at least one conductive pad and the at least one microneedle electrode array are further disposed in low-impedance electrical communication.

20. The microneedle electrode patch of claim 18, wherein the at least one conductive trace extends laterally from the at least one conductive pad.

21. A microneedle electrode system, comprising:
a microneedle electrode patch, comprising:
a first flexible substrate having a surface, a lateral edge and a plurality of conductive pads disposed on the surface, wherein each of the plurality of conductive pads further comprises a conductive trace extending therefrom and terminating proximate to the lateral edge of the first flexible substrate at an electrical contact,
a plurality of microneedle electrode arrays, wherein each microneedle electrode array is formed from a conductive substrate having a plurality of microneedles extending from at least a portion of an upper surface thereof and a lower surface disposed in contact with a corresponding one of the plurality of conductive pads on the first flexible substrate, wherein each microneedle electrode array further comprises a coating, and
a second flexible substrate having a plurality of openings defined therein dimensioned to accommodate at least the portion of each upper surface of the microneedle electrode array from which the plurality of microneedles extend;
wherein the plurality of conductive pads and the plurality of microneedle electrode arrays are disposed in electrical communication and the first flexible substrate and the second flexible substrate are bonded together such that each one of the plurality of microneedle electrode arrays extends through a corresponding one of the plurality of openings defined in the second flexible substrate; and
external electronics connected to the electrical contact of each of the plurality of microneedle electrode arrays, wherein the external electronics are adapted to at least one of stimulate or record electrical activity of each microneedle electrode array;
wherein each of the plurality of microneedle electrode arrays is individually addressable and wherein, in operation, the microneedle electrode arrays are adapted to be selectively functionally integrated to form an effective electrode, and wherein the plurality of microneedles are sized and shaped to pierce the stratum granulosum of mammalian skin.

22. The microneedle electrode system of claim 21, wherein the surface of the first flexible substrate further comprises an upper surface.

23. The microneedle electrode system of claim 21, wherein the plurality of conductive pads and the plurality of microneedle electrode arrays further disposed in low-impedance electrical communication.

24. The microneedle electrode system of claim 21, wherein the conductive trace extends laterally from each of the plurality of conductive pads.

25. The microneedle electrode system of claim 21, wherein the first flexible substrate comprises a polymer.

26. The microneedle electrode system of claim 21, wherein the second flexible substrate comprises a polymer.

27. The microneedle electrode system of claim 21, wherein the conductive substrate is at least partially formed from the group consisting of a metal and a polymer.

28. The microneedle electrode system of claim 27, wherein the metal is stainless steel.

29. The microneedle electrode system of claim 27, wherein the polymer is selected from the group consisting of poly methyl methacrylate, polyurethane, SU-8, polylactic acid, polylactic-co-glycolic acid, and polyethylene glycol.

30. The microneedle electrode system of claim 21, wherein the coating is a metal.

31. The microneedle electrode system of claim 21, wherein the coating is a low-impedance porous material.

32. The microneedle electrode system of claim 31, wherein the low-impedance porous material is selected from the group consisting of Ag/AgCl, nanoporous Pt, PEDOT:PSS, polyaniline, titanium nitride, and indium tin oxide.

33. The microneedle electrode system of claim 21, wherein the conductive trace further comprises an electrical contact proximate the lateral edge of the first flexible substrate adapted to connect to at least one of stimulation and recording electronics.

34. A microneedle electrode system, comprising:
a microneedle electrode patch, comprising:
a first flexible substrate having a surface, a lateral edge and a plurality of conductive pads disposed on the surface, wherein each of the plurality of conductive pads further comprises a conductive trace extending therefrom and terminating proximate to the lateral edge of the first flexible substrate at an electrical contact,
a plurality of microneedle electrode arrays, wherein each microneedle electrode array is formed from a conductive substrate having a plurality of microneedles extending from at least a portion of an upper surface thereof and a lower surface disposed in contact with a corresponding one of the plurality of conductive pads on the first flexible substrate, wherein each microneedle electrode array further comprises a coating, and
a second flexible substrate having a plurality of openings defined therein dimensioned to accommodate at least the portion of the upper surface of each microneedle electrode array from which the plurality of microneedles extend;
wherein the plurality of conductive pads and the plurality of microneedle electrode arrays are disposed in electrical communication and the first flexible substrate and the second flexible substrate are bonded together such that each one of the plurality of microneedle electrode arrays extends through a corresponding one of the plurality of openings defined in the second flexible substrate; and
external electronics connected to the electrical contact of each of the plurality of microneedle electrode arrays wherein the external electronics are adapted to at least one of stimulate or record electrical activity of each microneedle electrode array;
wherein each of the plurality of microneedle electrode arrays is individually addressable and wherein, in operation, the microneedle electrode arrays are adapted to be selectively functionally integrated to form an effective electrode, and wherein the plurality of microneedles have a height of from about 100 to about 1000 micrometers above the upper surface of each microneedle electrode array.

35. The microneedle electrode system of claim 34, wherein the plurality of conductive pads and the plurality of microneedle electrode arrays are further disposed in low-impedance electrical communication.

36. The microneedle electrode system of claim 34, wherein the conductive trace extends laterally from each of the plurality of conductive pads.

37. A method for using a microneedle electrode system, comprising:
providing a microneedle electrode system, comprising:
a microneedle electrode patch, comprising:
a first flexible substrate having a surface, a lateral edge and a plurality of conductive pads disposed on the surface, wherein each of the plurality of conductive pads further comprises a conductive trace extending therefrom and terminating proximate to the lateral edge of the first flexible substrate at an electrical contact,
a plurality of microneedle electrode arrays, wherein each microneedle electrode array is formed from a conductive substrate having a plurality of microneedles extending from at least a portion of an upper surface thereof and a lower surface disposed in contact with a corresponding one of the plurality of conductive pads on the first flexible substrate, wherein each microneedle electrode array further comprises a coating, and
a second flexible substrate having a plurality of openings defined therein dimensioned to accommodate at least the portion of the upper surface of each microneedle electrode array from which the plurality of microneedles extend;
wherein the plurality of conductive pads and the plurality of microneedle electrode arrays are disposed in electrical communication and the first flexible substrate and the second flexible substrate are bonded together such that each one of the plurality of microneedle electrode arrays extends through a corresponding one of the plurality of openings defined in the second flexible substrate; and
external electronics connected to the electrical contact of each of the plurality of microneedle electrode arrays, wherein the external electronics are adapted to at least one of stimulate or record electrical activity of each microneedle electrode array;
wherein each of the plurality of microneedle electrode arrays is individually addressable and wherein, in operation, the microneedle electrode arrays are adapted to be selectively functionally integrated to form an effective electrode, wherein the plurality of microneedles are sized and shaped to pierce the stratum granulosum of mammalian skin;
applying the microneedle electrode patch to a target region comprising at least one nerve and a muscle;
selectively stimulating a first portion of the plurality of microneedle electrode arrays; and
selectively recording an evoked electrical activity from at least a second portion of the plurality of microneedle electrode arrays.

* * * * *